(12) United States Patent
Thu et al.

(10) Patent No.: US 6,336,047 B1
(45) Date of Patent: Jan. 1, 2002

(54) COMMUNICATION SYSTEM BETWEEN TRAINING SENSOR AND ELECTRODES OF A DEFIBRILLATOR

(75) Inventors: Kjell R. Thu, Bryne; Harald Vatne, Naerbo; Hakon Hodne, Kleppe; Helge Fossan; Helge Myklebust, both of Stavanger, all of (NO)

(73) Assignee: Laerdal Medical AS, Stavanger (NO)

( * ) Notice: Subject to any disclaimer, the term of this patent is extended or adjusted under 35 U.S.C. 154(b) by 0 days.

(21) Appl. No.: 09/386,841

(22) Filed: Aug. 31, 1999

(30) Foreign Application Priority Data

Sep. 15, 1998 (NO) .................................................. 4269

(51) Int. Cl.$^7$ ................................................ A61N 1/18
(52) U.S. Cl. ............................. 607/5; 434/265; 607/30; 607/75; 607/142
(58) Field of Search ................................ 434/262, 265; 607/4, 5, 6, 8, 30, 75, 142

(56) References Cited

U.S. PATENT DOCUMENTS

| | | | |
|---|---|---|---|
| 4,611,998 A | * | 9/1986 | Ramamurthy ............... 434/265 |
| 5,137,458 A | * | 8/1992 | Ungs et al. .................. 434/262 |
| 5,853,292 A | * | 12/1998 | Eggert et al. ................ 434/262 |
| 5,993,219 A | * | 11/1999 | Bishay ........................ 434/265 |

FOREIGN PATENT DOCUMENTS

| | | |
|---|---|---|
| EP | 0 437 339 | 7/1991 |
| EP | 0 499 744 | 8/1992 |
| GB | 2 339 323 | 1/2000 |

* cited by examiner

Primary Examiner—Jeffrey R. Jastrzab
Assistant Examiner—Frances P. Oropeya
(74) Attorney, Agent, or Firm—Nixon & Vanderhye P.C.

(57) ABSTRACT

A system for communication between sensors in training equipment and electrodes for a defibrillator (AED) or a defibrillator-trainer (AED-T) provides for determining electrode positioning and providing feedback to the user. The training equipment is provided with a non-conductive chest skin, and the communication is wireless and bi-directional. The information from the manikin is generated by a microprocessor with a digital-analog converter. The information signal is transmitted to the sensors in the manikin by use of drivers, which sensors each constitute one half of a non-galvanic coupling, in which the chest skin separates the halves, and the other halves of the non-galvanic couplings are formed by electrodes that are attached to the chest skin, the non-galvanic coupling being in the form of capacitors or coils.

11 Claims, 5 Drawing Sheets

COMMUNICATION SYSTEM BETWEEN TRAINING SENSOR AND ELECTRODES OF A DEFIBRILLATOR

BACKGROUND

The present invention relates to a system for communication between sensors in training devices and the electrodes of an AED or an AED-T for the purpose of determining electrode positioning and providing feedback to the user.

For years, the use of AEDs in the case of sudden cardiac death has been recognized as the only curative treatment. Defibrillation involves the discharge of an electric pulse with relatively high energy through electrodes connected to the patient's chest. Several designs of electrodes exist, but generally they can be divided into two groups: "Paddles" are electrodes that are held manually on the chest. Adhesive electrodes or "Pads" are electrodes that are attached to the chest by the use of a conducting adhesive.

The electrodes are used both to discharge the electrical shock, to measure the patient's ECG, and to measure any impedance.

Defibrillation may, by its very nature, involve a risk for those who treat the patient, if they touch the patient or in any other way come into contact with the electrodes.

Traditionally, defibrillation has been carried out by highly trained personnel in hospitals. However, AEDs have become much easier to use over the last ten years, and thus have also come to be used outside of the hospitals, primarily by the ambulance services. There is also a clear tendency for defibrillators to be used by the laity before the ambulance reaches the patient.

This means that there is a great need for training the users of defibrillators. Such training systems are available, and mainly consist of a training manikin and an electronic simulator. The defibrillator patient cable is connected to contact points on the chest of the manikin, and the simulator simulates typical heart rhythms, in addition to handling and registering the electric shock. The manikin and/or AED may also contain a report producer, which registers and reports the treatment that is being carried out.

In such a training system, the connection of the electrode takes place through galvanic coupling between the manikin and the AED, normally without the use of defibrillation electrodes. The ECG signal that is generated by the simulator is transmitted to the AED through the electrode connections, and the electric shock being discharged from the AED is transmitted the other way, to the manikin. The connections on the manikin must then have a typical patient impedance of approximately 50 Ohm, which must be able to absorb the relatively high energy from the AED. Beyond this, there is no direct communication between the manikin and the AED.

This has several disadvantages: Visible contact points are used for connecting the AED. This means that there is no opportunity for practicing realistic placement of electrodes based on anatomical references, or for practicing the manipulation that is required for effective connection and placement of the electrodes.

When the AED is used, it will normally give off an energy pulse of between 200 Joules and 360 Joules. The disadvantage of this is that the electronics in the manikin must handle both high voltages and high outputs, which makes the solution both large and costly. A further disadvantage is the fact that students may be exposed to high voltages, something that constitutes a safety risk. The fact that the energy is drawn from the AED battery is another disadvantage, as more and more AEDs are equipped with expensive, non-rechargeable primary batteries based on lithium.

There are AED-Ts available that do not have the disadvantages of high voltage and expensive lithium batteries. These devices do not interact with the manikin, and will operate in the same manner whether the electrodes are connected to the manikin or not.

AEDs that can run their own training software are also available. In this mode, the AED will not use the high voltage system, instead it will simulate the discharge of electric shocks and the measurements of the electrical activity of the heart. These devices have no interaction with the manikin either, and will operate in the same manner whether the electrodes are connected to the manikin or not.

Thus, an AED/AED-T is not able to indicate whether the electrodes have been placed correctly and have sufficient contact. Also, the manikin can not automatically be set to generate a noticeable pulse upon receiving a simulated electric shock.

It is essential to patient treatment that the electrodes be placed in the correct position on the patient, so as to deliver sufficient energy to the heart muscle. This correct emplacement is dependent on the user having been trained correctly, e.g., by practicing on a manikin.

Training equipment with the possibility of positioning AED electrodes is known from U.S. Pat. No. 5,137,458. In this, use has been made of Hall-effect sensors arranged in groups, with a permanent magnet and a monitor attached to the manikin for determination of the electrode positions, and for providing feed-back regarding the correct/incorrect placement of the electrodes.

U.S. Pat. No. 5,662,690 and U.S. Pat. No. 5,611,815 describe an AED that maybe set manually to two modes: training or treatment. The option of automatic detection of the state of connection between the AED and the training equipment is not mentioned in these patents. U.S. Pat. No. 5,275,572 describes training electrodes that are glued to the skin on a manikin's chest, and further connect ed to an ECG simulator via cables.

SUMMARY OF THE INVENTION

The present invention aims to avoid the above mentioned disadvantages.

Further, the present invention aims to provide non-galvanic communication between the AED/AED-T and the training equipment, e.g. through the skin on the chest of the manikin, as well as detection of electrode positioning on the chest.

The present invention also aims to enable an AED to automatically measure whether it is connected to training equipment or to a patient.

BRIEF DESCRIPTION OF THE DRAWINGS

The following describes the invention in greater detail, with reference to the drawings, in which.

DETAILED DESCRIPTION OF PREFERRED EMBODIMENTS

Figure 1:
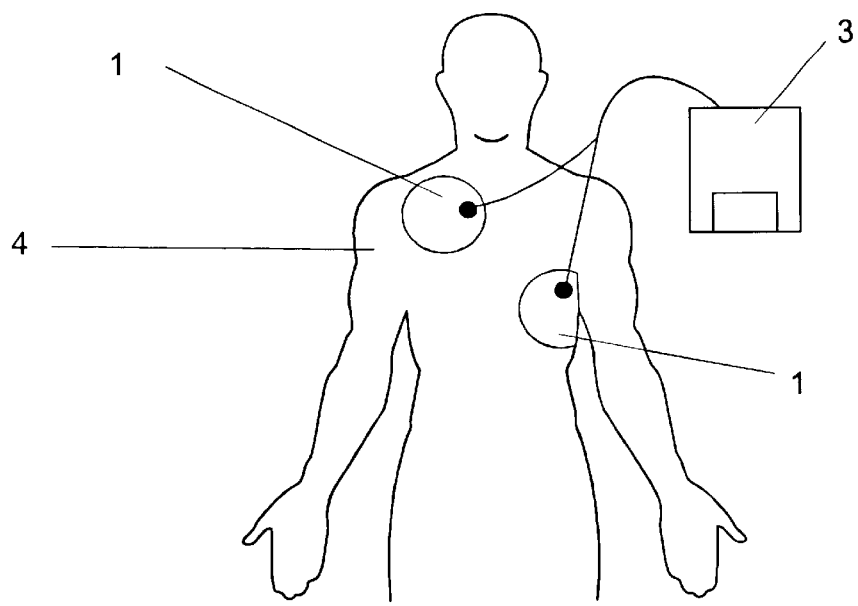
FIG. 1 schematically shows a manikin with the adhesive electrodes of an AED/AED-T.

FIG. 1 indicates a manikin 4, to which electrodes 1 have been attached by an adhesive, in a manner that in itself is known. The electrodes 1 are directly connected to an AED/AED-T 3.

The purpose of the communication is to simulate the use of a real AED on a patient, by using the training equipment. This is done by communicating simulated physiological parameters and actions on the training equipment to the AED/AED-T, and by communicating the operation of the AED/AED-T to the training equipment.

The following are examples of the type of information that may be exchanged: Status/type of ECG, simulated ECG signal in real time, checking of unconsciousness, palpating pulse, free respiratory passages in the manikin after bending the head back and/or lifting the jaw, quality of HLR including depth/rate of compressions and rate/volume of ventilations, blowing-in time, hand positioning in the case of heart compression, synchronous or asynchronous pulse, medication-type, amount, time and place of injection, infusion-type, amount, time and place of infusion, electrode connection including electrode positioning, delivered electric shock, control of simulated muscle spasms at shock delivery, spontaneous breathing, chest movements, electric shock energy, $SpO_2$-value, end-tidal $CO_2$, blood pressure reading, all operating parameters of the AED and the training equipment, physiological body sounds, automatic switching of the training equipment between on and off, and automatic switching of the AED between on and off.

It is envisaged that the communication will take place primarily over electrodes that are glued or otherwise attached to the chest of the manikin, the skin of which is made from a non-conductive material, so that all communication can be wireless and take place between the electrodes and the sensors in the training equipment; or there may be direct wireless communication between the training equipment and the AED/AED-T independently of the electrodes, where the electrodes transmit a signal in the form of a signature that indicates contact between the sensors and the electrodes, and which initiates another direct, wireless communication.

Both special training electrodes and treatment electrodes may be used. These are connected to the AED/AED-T 3 by means of a cable, and are glued or otherwise attached to the manikin's 4 chest. Sensors 2 are placed on the underside of the manikin's 4 chest, in order to measure the positioning of the electrodes 1 and communicate wirelessly with the electrodes 1.

Figure 2:
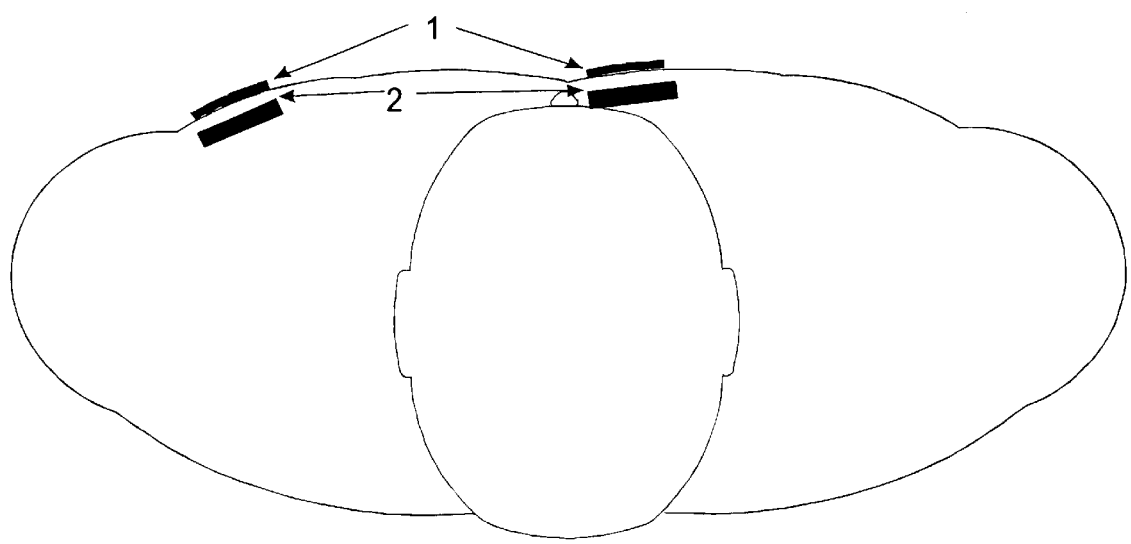
FIG. 2 schematically shows a capacity coupling between sensors and electrodes.

This can be implemented through a capacity coupling, in which the electrode 1 acts as one disc of a capacitor and the sensor 2 acts as the other disc, see FIG. 2.

It may also be solved by the use of inductance, where the sensor 2 in the manikin is a coil with one or more turns. The electrode 1 can also be designed as a coil for use in communication, or it may be a metallic foil, see FIG. 3.

Figure 4:
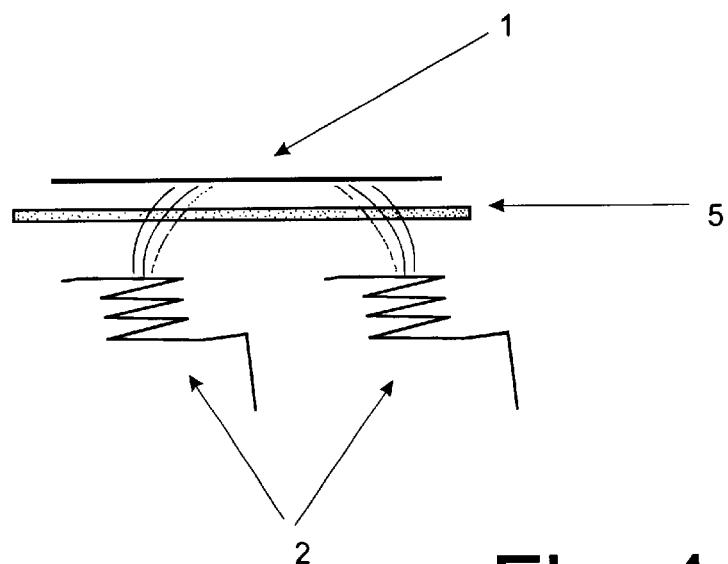
FIG. 4 schematically shows a coil coupling between sensors and electrodes.

The electrode 1 may also act as a connection between several coils 2 placed in or on the inside of the skin on the manikin's 5 chest. (FIG. 4).

Figure 3:
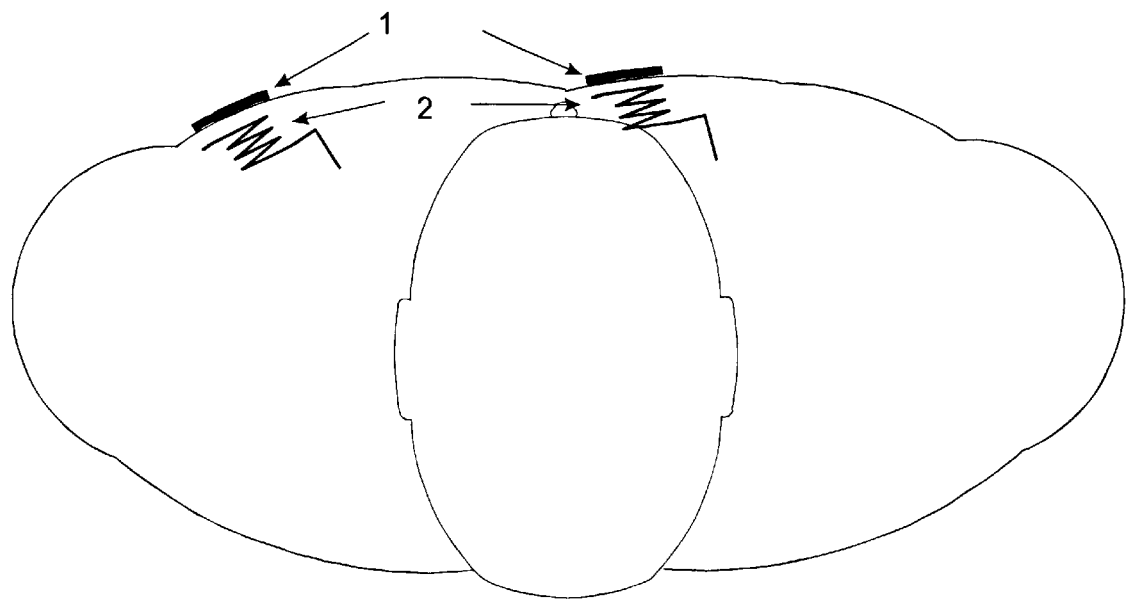
FIG. 3 schematically shows an inductance coupling between sensors and electrodes.

In order to measure the positioning of the electrodes, the electrode 1 and the sensor 2 may be constructed with only one connecting element, see the examples in FIG. 2 and FIG. 3. Here, it will be possible to measure the degree of connection between the electrode 1 and the sensor 2, and then to determine an approximate electrode positioning based on this. Such a measurement is known in itself, and those skilled in the art will know how to implement it.

Figure 5:
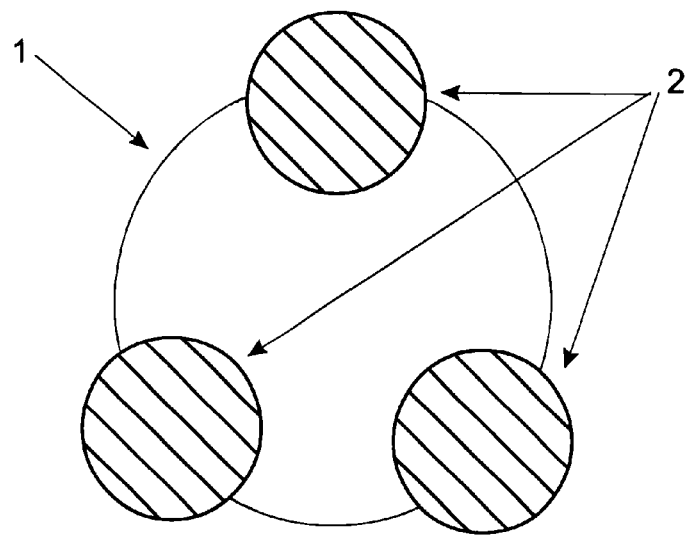
FIG. 5 schematically shows an example of position measuring.

FIG. 5 schematically shows an example where the electrode 1 and the sensor 2 are constructed with several connecting elements. Here, it will be possible both to measure the degree of connection between the electrode 1 and the sensor 2, and determine the exact positioning of the electrode.

Figure 6:
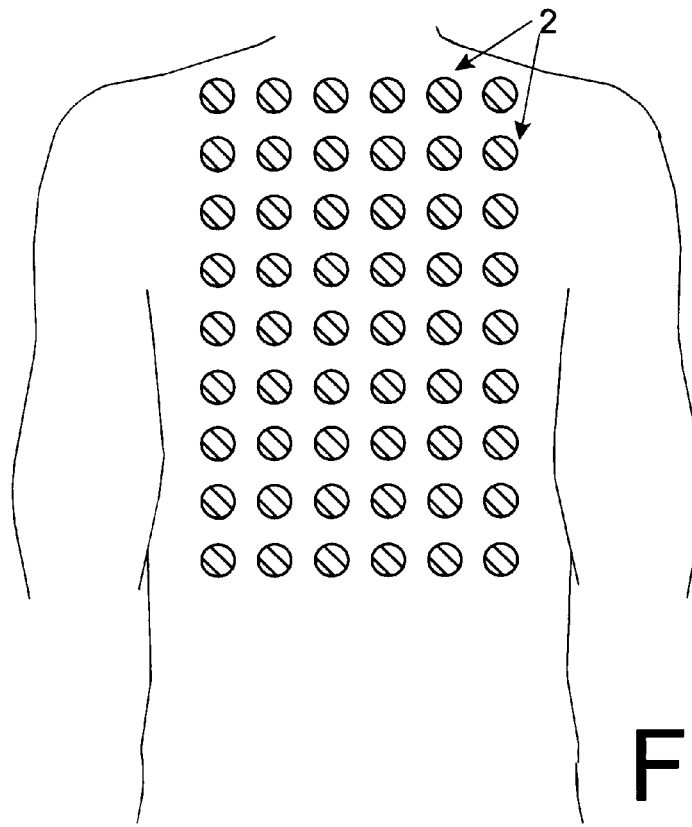
FIG. 6 schematically shows a matrix arrangement of sensors.

A solution may also be envisaged where the entire chest skin is a matrix of sensors, see FIG. 6. It will then be possible to determine electrode positions across the entire area of the chest.

Figure 7:
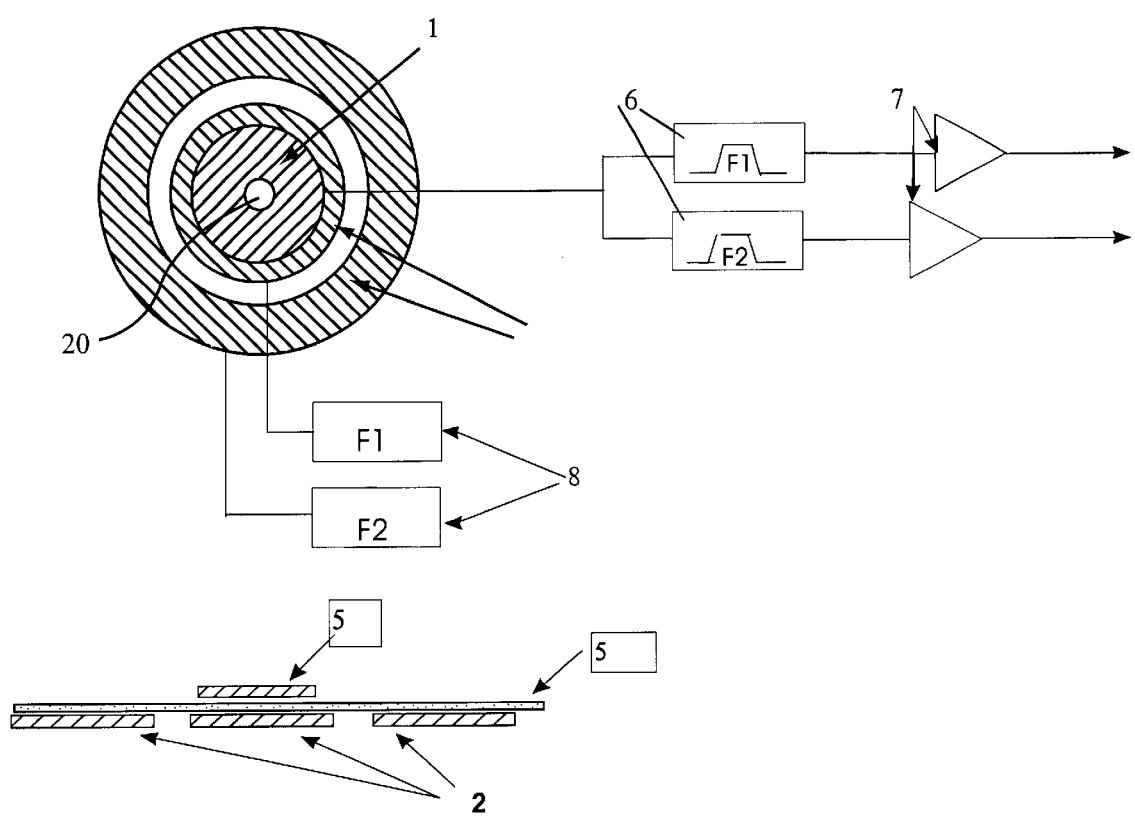
FIG. 7 schematically shows an example of determination of electrode positioning by the use of two frequencies.
Figure 8:
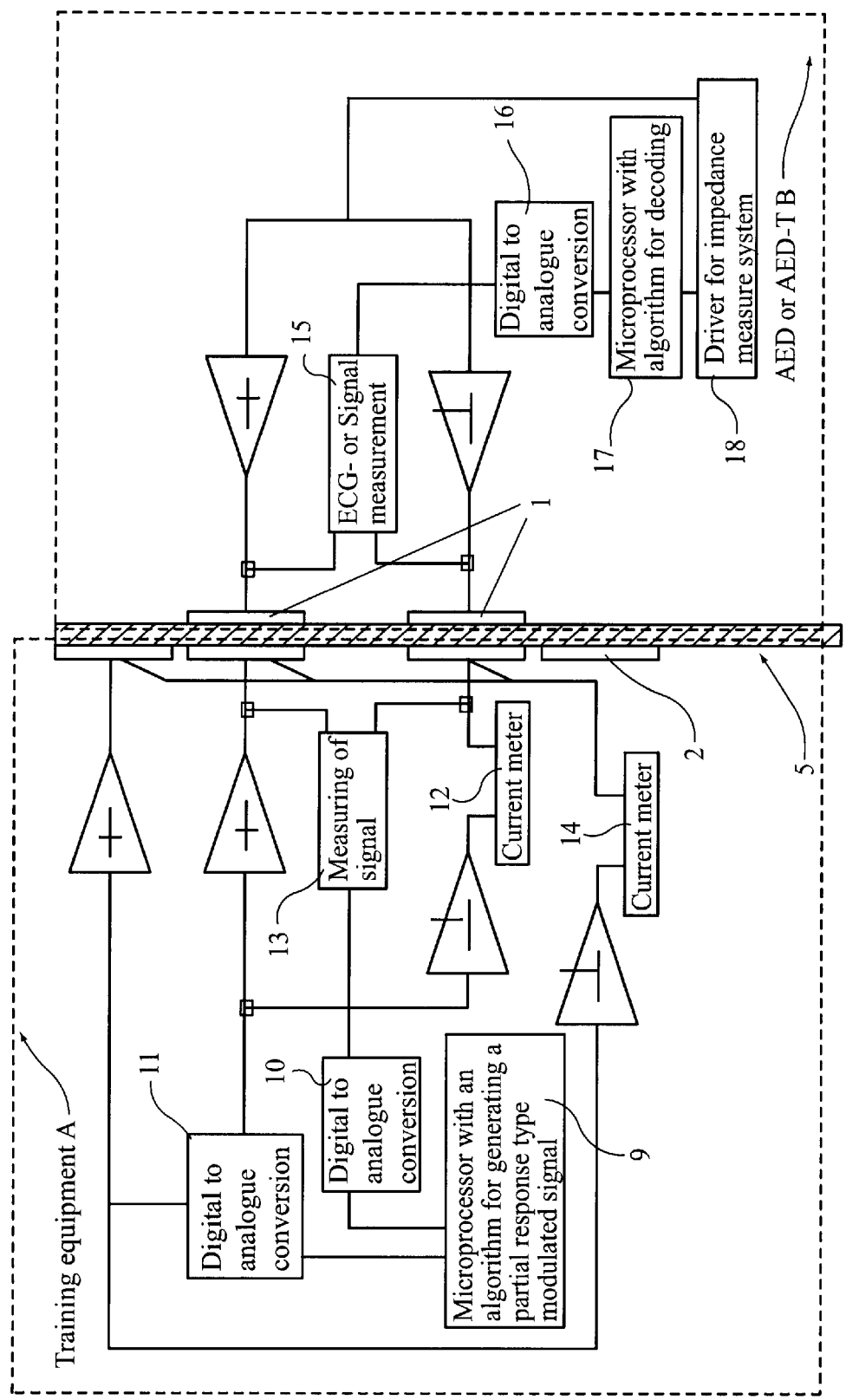
FIG. 8 schematically shows a conceptual drawing of the preferred embodiment.

A sensor 2 may consist of two concentric faces, which do not overlap each other, see FIG. 7. These faces are connected to respective oscillators 8 that emit two different frequencies. When the AED by means of band-pass filters 6 and amplifiers 7 detects one of these frequencies on one electrode, it will automatically go into training mode. The ratio between the signal strength from the amplifiers 7 after the band-pass filters 6 will give information regarding electrode positioning.

A solution may also be envisaged where these methods are used for measuring the position of the electrodes only, and where all communication between the manikin and the AED takes place through a wireless medium, across another interface.

This may be in the form of radio communication, where for example the electrode cables are used as an antenna. Other antenna solutions may also be envisaged.

Alternatively, other forms of communication may be used, such as light, primarily in the form of IR light, or sound, primarily in the form of ultrasound.

Any form of analog or digital modulation may be used for wireless communication, e.g., FM, AM, CW, BPSK (Binary Phase Shift Keying), QPSK (Quadrature Phase Shift Keying), FSK (Frequency Shift Keying), M-FSK (M-ary Frequency Shift Keying).

The receiver in the AED may in its simplest form use the ECG amplifier as a receiver for the signals from the manikin. The ECG amplifier may have several modes of operation, in which it changes the frequency characteristics when in training mode, so as to be able to transmit relatively high frequency signals.

The transmitter in the AED may in its simplest form consist of a shock delivery circuit with several modes of operation, in which it delivers harmless and electrically safe micropulses when in training mode.

Known systems for measuring impedance and systems for connecting electrodes may also be used as a transmitter in the AED. These systems are normally based on a low alternating current being sent through the patient electrodes. Obviously, the AC-current may also be used to communicate with the manikin, in a modulated or non-modulated form.

AEDs often use relay connections for delivering electroshocks. Switching this relay connection on and off will cause a change in impedance in the AED patient circuit. This change in impedance may also be used for communication between the AED and the manikin.

The transmitter and the receiver may also be realized as circuit solutions that are independent of the ECG amplifier, the shock delivery circuit and the systems for measuring impedance.

In a preferred embodiment, the training equipment A is provided with a microprocessor 9 with an algorithm for generating a partial response type modulated signal. Following a digital to analog conversion 11, this signal is transmitted to respective drivers, in order to drive the signal symmetrically for each of the sensors 2 in the training equipment A. These sensors 2 are attached to the inside of a non-conductive chest skin 5, and each of the sensors form half of a capacitor, in which the chest skin 5 of the training equipment 5 forms the insulation between the capacitor discs. The electrodes 1 belonging to a defibrillator (AED) or a defibrillator-trainer (AED-T) form the other half of the capacitor discs. If the equipment that is connected up is an AED, the existing ECG inlet 15 or inlet for impedance measurement signal 15 is used as a receiver for the communication signal. If the equipment that is connected up is an AED-T, the electrodes 1 will be connected to a signal meter 15, which is further connected to an analog-digital converter 16, and thereafter to a microprocessor 17, in which the signal is demodulated.

As use of the training equipment will result in movement between the electrodes 1 and the sensors 2, and thereby in variable capacitance, a current meter 12, 14 has been put in the training equipment A, which meter transmits a signal to the microprocessor 9 (not shown). The electric signal uses the microprocessor 9 to control the biasing, to ensure that the communication signal maintains approximately equal strength between the electrodes 1.

Each of the sensors in the manikin consists of a flexible, electrically conductive area, with a diameter of 5–15 cm. Around each sensor is another electrically conductive area. These areas have been positioned to form the non-valid areas of electrode positioning. A signal with a fixed signature S2 or frequency F2 is transmitted to these areas, whereas a signal with a fixed signature S1 or frequency F1 is transmitted to each sensor. Correct placing of the electrodes is determined according to the ratio between S1 and S2 or according to the ratio between F1 and F2, and this can be measured both by the current meter 12, 14 in the training equipment A and by the signal meter in the ECG measuring system in the AED B.

In order to indicate the correct placement of the electrodes, a light source 20 (FIG. 7) has been provided in the center of each sensor. This is not normally visible or noticeable. When the light source lights up, it will shine through the chest skin when this is made of PP, PE, TPE, PVC or silicone materials and the thickness is 1 mm–6 mm.

The communication signal from the AED to the training equipment is the signal belonging to the system, which is measuring the impedance 18, modulated from the microprocessor 17 in the AED. From an AED-T, this signal will consist of a modulated signal with a basic frequency of between 500 Hz and 500 kHz. The communication signal is transmitted capacitively from the electrodes to the sensors in the training equipment. The signal meter 13 in the training equipment will transmit the signal to an analog-digital converter 10, from which the signal goes to the microprocessor for demodulation.

What is claimed is:

1. A system for communication between sensors in training equipment and electrodes of a defibrillator or a defibrillator-trainer, collectively hereinafter "defibrillator," the training equipment including a manikin on which an electrode can be placed for determining electrode positioning and providing feedback to the user, the system comprising:

a plurality of sensors attachable to an inside surface of the manikin, the sensors effecting a wireless and bi-directional communication signal for communication with the defibrillator, wherein the sensors each comprise a first half of a non-galvanic coupling that determines a signal path for the communication signal; and a second half of the non-galvanic coupling including the electrodes of the defibrillator, the second half being attachable to an outside surface of the manikin.

2. A system according to claim 1, wherein the training equipment further comprises an emitting device that emits a first identification signal that causes the defibrillator to set itself to a training mode.

3. A system according to claim 1, wherein the defibrillator further comprises an emitting device that emits a second identification signal to the training equipment, the training equipment returning the second identification signal to the defibrillator in a state that is dependent on an operating mode of the training equipment.

4. A system according to claim 1, further comprising an indicator disposed relative to the electrodes of the defibrillator, the indicator showing a positioning of the electrodes.

5. A system according to claim 4, wherein the indicator is a light.

6. A system according to claim 1, wherein the non-galvanic coupling is capacitive.

7. A system according to claim 1, wherein the non-galvanic coupling is inductive.

8. A system according to claim 1, wherein each of the sensors comprises two concentric faces, each connected to an oscillator that emits different frequencies, respectively, wherein the defibrillator goes into a training mode upon detecting one of the different frequencies.

9. A system according to claim 8, wherein the different frequencies are output to amplifiers via corresponding band-pass filters, the electrode positioning being determined based on a ratio of output from the amplifiers, respectively.

10. A system according to claim 8, further comprising current meters that measure the output from the amplifiers.

11. A communication system for defibrillator training equipment including a manikin on which an electrode can be placed for determining electrode positioning and providing feedback to the user, the communication system comprising:

a plurality of first sensors attachable to an inside surface of the manikin; and a plurality of second sensors comprising electrodes of a defibrillator or a defibrillator-trainer, collectively hereinafter "defibrillator," wherein the first sensors and the second sensors define respective capacitive couplings that are configured to effect wireless two-way data communication between the manikin and the defibrillator.

* * * * *